US009562909B2

(12) United States Patent
Fukuda et al.

(10) Patent No.: US 9,562,909 B2
(45) Date of Patent: Feb. 7, 2017

(54) SENSOR USED FOR MEASURING BIOLOGICAL INFORMATION ON USER

(71) Applicant: ARKRAY, Inc., Kyoto (JP)

(72) Inventors: Kazuo Fukuda, Kyoto (JP); Hisashi Kaneda, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 14/683,233

(22) Filed: Apr. 10, 2015

(65) Prior Publication Data

US 2015/0293112 A1   Oct. 15, 2015

(30) Foreign Application Priority Data

Apr. 15, 2014  (JP) ................................. 2014-83405
Feb. 23, 2015  (JP) ................................. 2015-32811

(51) Int. Cl.
```
G01N 33/00      (2006.01)
G01N 33/66      (2006.01)
G01N 33/487     (2006.01)
A61B 5/145      (2006.01)
A61B 5/1486     (2006.01)
G01N 27/327     (2006.01)
C12Q 1/00       (2006.01)
G01N 21/78      (2006.01)
```

(52) U.S. Cl.
CPC ............. *G01N 33/66* (2013.01); *A61B 5/1486* (2013.01); *A61B 5/14532* (2013.01); *G01N 27/3272* (2013.01); *G01N 33/4875* (2013.01); *G01N 33/48707* (2013.01); *C12Q 1/00* (2013.01); *G01N 21/78* (2013.01)

(58) Field of Classification Search
CPC .. G01N 33/66; G01N 33/48707; G01N 21/78; G01N 27/3272; A61B 5/14532
See application file for complete search history.

(56) References Cited

U.S. PATENT DOCUMENTS

2010/0021342 A1   1/2010   Joseph et al.
2011/0054275 A1   3/2011   Stafford

FOREIGN PATENT DOCUMENTS

| EP | 1961382 A1 | 8/2008 |
|----|-----------|--------|
| EP | 2117421 A1 | 11/2009 |
| JP | 4085137 B2 | 5/2008 |
| JP | 2012-18010 A | 1/2012 |
| WO | 2008/085251 A1 | 7/2008 |

OTHER PUBLICATIONS

Extended European Search Report issued in corresponding European Patent Application No. 15163743.6 dated Sep. 9, 2015.

*Primary Examiner* — Sam P Siefke
(74) *Attorney, Agent, or Firm* — Morgan, Lewis & Bockius LLP

(57) ABSTRACT

A sensor includes a substrate that includes an upper substrate and a lower substrate, and an electrode that is provided on the lower substrate, and the upper substrate, the lower substrate, and the electrode are formed by an optically transparent member.

4 Claims, 13 Drawing Sheets

Example of guideline

Insufficient sample:
flash in blue

Measurement
preparation is complete:
light in blue

Example of error display

Measurement error:
flash in red

SENSOR USED FOR MEASURING BIOLOGICAL INFORMATION ON USER

CROSS-REFERENCE TO RELATED APPLICATION

This application is based upon and claims the benefit of priority from Japanese patent application No. 2014-83405, filed on Apr. 15, 2014, and Japanese patent application No. 2015-32811, filed on Feb. 23, 2015 the disclosure of which are incorporated herein in its entirety by reference.

BACKGROUND OF THE INVENTION

1. Field of the Invention

The present invention relates to a sensor and a measuring apparatus, and in particular to a sensor and a measuring apparatus for measuring biological information on a user using a reagent.

2. Description of Related Art

In recent years, in the field of medical analysis, a disposable analyzer in which a sample is supplied to a sensor has been widely used, due to ease of handling. For example, with a small mobile blood glucose meter, blood that serves as a sample is introduced by suction into a capillary formed in a small strip-like sensor, and reacts with a reagent that has been provided inside the sensor in advance. Moreover, an electric current value is measured by electrochemically measuring a reagent component that has reacted with glucose in the blood, and the measured electric current value is applied to a calibration curve to calculate a blood glucose level. Also, the blood glucose meter displays the calculated blood glucose level on a screen or the like.

Increase in usage of such a sensor has been accompanied by user demand for improvement in the usability of the sensor. For example, Japanese Patent No. 4085137 (Patent Document 1) discloses a measuring apparatus that includes a light source that illuminates a portion of a sensor to which a sample is supplied in order to easily supply the sample to the sensor in a dark place.

Also, for example, JP 2012-18010A (Patent Document 2) discloses a measuring apparatus (a blood glucose meter) that causes a display to display a glucose level in blood, and that emits light of a color corresponding to the glucose level from a backlight of the display at the same time. It is conceivable that according to the measuring apparatus disclosed in Patent Document 2, a user is able to immediately know whether his or her blood glucose level is normal, and therefore, usability will be significantly improved.

However, in the case where the measuring apparatus is a blood glucose meter, the user is usually a patient suffering from diabetes and often has poor eyesight, and thus, usability of the measuring apparatus disclosed in Patent Document 1 is not sufficiently improved.

On the other hand, according to the measuring apparatus disclosed in Patent Document 2, although usability is significantly improved, it is necessary to use a backlight that can emit light of a plurality of colors as a backlight of the display. Therefore, the measuring apparatus disclosed in Patent Document 2 is problematic in that the manufacturing cost is high.

SUMMARY OF THE INVENTION

This invention was made to solve the above-described issues, and an object thereof is to provide a sensor and a measuring apparatus whose usability for a user is improved and with which an increase in manufacturing cost can be suppressed.

A sensor according to the present invention is a sensor that is to be used for measuring biological information on a user, and the sensor includes a substrate that includes an upper substrate and a lower substrate, and an electrode that is provided on the lower substrate, and the upper substrate, the lower substrate, and the electrode are formed by an optically transparent member.

According to the sensor having such a configuration, it is possible to cause the sensor to shine by illuminating the sensor itself, and thus, for example, as a result of changing the emission mode of light at that time in accordance with the measurement result or the like, the measurement result or the like can be intuitively understood due to light emitted from the sensor. Also, because the user often pays attention to the sensor when supplying a sample to the sensor, usability for him or her is further increased by notifying the measurement result or the like by causing the sensor to shine. Furthermore, because it is not necessary to provide a display or the like that can emit light of a plurality of colors, an increase in manufacturing cost can be suppressed.

Also, in the sensor of the present invention, the substrate may display identification information of the sensor by a pattern formed by using at least one of a transmitting portion that allows light entering the substrate to pass through and a light-blocking portion that blocks light entering the substrate.

According to the sensor having such a configuration, for example, because identification wiring can be formed in the same manufacturing step as that for sensor wiring, identification information can be displayed for each sensor using a simple configuration without making holes in a substrate using a different pattern.

Also, in the sensor of the present invention, the electrode may include a first electrode that is formed on one face of the substrate and a second electrode that is formed on another face of the substrate, and the first electrode and the second electrode may be electrically connected to each other via a through hole that passes through the substrate.

According to the sensor having such a configuration, when the sensor is used, a user can check that a sample has been introduced by suction from either the front side or the back side, and thus, usability for him or her is further improved.

Also, in the sensor of the present invention, the substrate may be configured to further include a reflective portion that reflects light entering the substrate.

According to the sensor having such a configuration, even in the case where a user has poor eyesight, he or she can easily check information relating to the sensor.

Also, in the sensor of the present invention, at least a portion of an edge of the substrate may be colored.

According to the sensor having such a configuration, the sensor can be caused to stand out even if the substrate and the electrode are formed by an optically transparent member, and thus, it is possible to prevent the sensor from being lost and to easily see the shape of the sensor.

A measuring apparatus according to the present invention is a measuring apparatus that measures biological information on a user using a sensor in which an upper substrate and a lower substrate that are included in a substrate, and an electrode that is provided on the lower substrate are formed by an optically transparent member, and the measuring apparatus includes a main body in which an insertion opening is provided for insertion of the sensor, and a first light source that is provided inside the main body and illuminates the sensor.

According to the measuring apparatus having such a configuration, it is possible to cause the sensor to shine by illuminating the sensor itself, and thus, for example, as a result of changing the emission mode of light at that time in accordance with the measurement result or the like, the measurement result or the like can be intuitively understood due to light emitted from the sensor. Also, because the user often pays attention to the sensor when supplying a sample to the sensor, usability for him or her is further increased by notifying the measurement result or the like by causing the sensor to shine. Furthermore, because it is not necessary to provide a display or the like that can emit light of a plurality of colors, an increase in manufacturing cost can be suppressed.

Also, the measuring apparatus of the present invention may further include, on the substrate of the sensor, an identification information reading unit for reading identification information that is indicated by a pattern formed by using at least one of a transmitting portion that allows light entering the substrate to pass through and a light-blocking portion that blocks light entering the substrate, and the identification information reading unit may include a second light source that emits light onto the pattern, a light-receiving portion that receives light that has passed through the pattern, and a specifying unit that specifies the identification information based on the light received by the light-receiving portion.

According to the measuring apparatus having such a configuration, for example, because identification wiring can be formed in the same manufacturing step as that for sensor wiring, it is possible to specify identification information of the sensor by distinguishing between the transmission of light and the blocking of light, without checking holes made in a substrate using a different pattern, or the like. In other words, it is possible to easily specify identification information for each sensor.

Also, in the measuring apparatus according to the present invention, the first light source may emit light in various emission modes in accordance with a measurement result of the measuring apparatus.

As described above, according to the present invention, it is possible to provide a sensor and a measuring apparatus whose usability for a user is improved and with which an increase in manufacturing cost can be suppressed.

The foregoing and other objects, features, aspects and advantages of the present invention will become more apparent from the following detailed description of the present invention when taken in conjunction with the accompanying drawings.

DETAILED DESCRIPTION OF THE INVENTION

Configuration

First, the configurations of a measuring apparatus 10 and a sensor 20 in an embodiment of the present invention will be described using FIGS. 1, 2A and 2B.

Configuration of Measuring Apparatus

First, the configuration of the measuring apparatus 10 in the embodiment of the present invention will be described using FIG. 1. FIG. 1 is a perspective view showing the external configuration of the measuring apparatus in the embodiment of the present invention.

Figure 1:
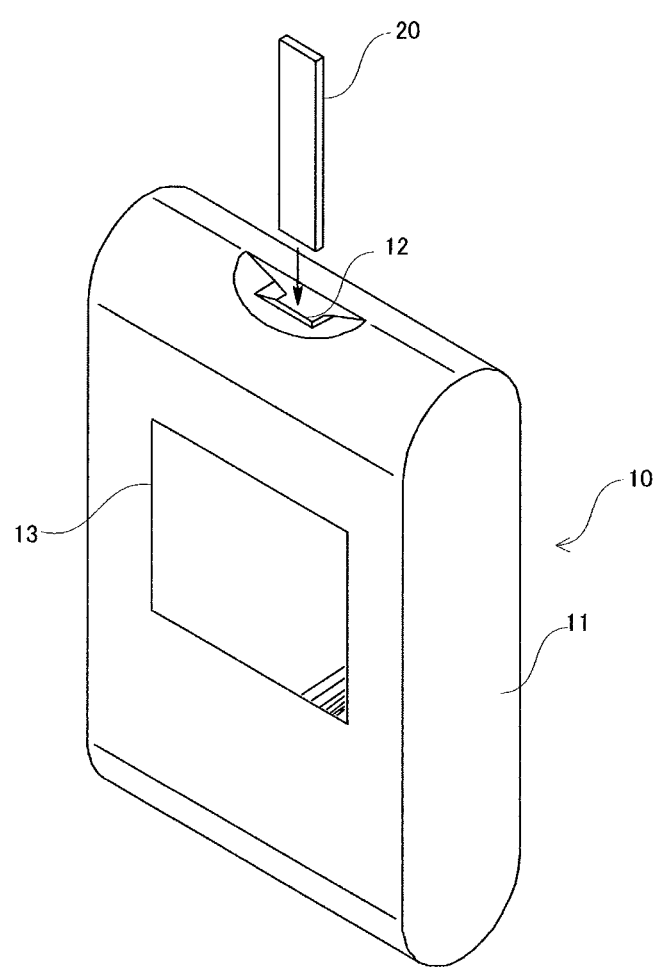
FIG. 1 is a perspective view showing an external configuration of a measuring apparatus according to an embodiment of the present invention.

As shown in FIG. 1, the measuring apparatus 10 is a medical device for measuring biological information on a user, and examples thereof include a blood glucose meter, a lactic acid meter, a ketone body measuring apparatus, a urine test strip meter, and a lipid measuring apparatus. The embodiment of the present invention will describe a case in which the measuring apparatus 10 is a mobile blood glucose meter for measuring the blood glucose level in the blood of a user.

The measuring apparatus 10 includes a main body 11, an insertion opening 12, and a display unit 13. A connection terminal is provided inside the insertion opening 12. In addition, in the present embodiment, a switch (not shown) of the main body 11 is turned on by the sensor 20 being inserted into the insertion opening 12, as a result of which the measuring apparatus 10 is started.

The sensor 20 has a small strip-like shape, for example, and accommodates a reagent and an electrode. When blood, which is the sample, that was collected from a user is introduced by suction into a capillary formed in the sensor 20, the reagent reacts with the blood inside the sensor 20.

If the reagent reacts with blood in a state in which the measuring apparatus 10 is on, the measuring apparatus 10 measures an electric current value by electrochemically measuring the reagent component that has reacted with glucose in blood, and applies the measured electric current value to a calibration curve to calculate the blood glucose level of the user. The measuring apparatus 10 then displays the measurement result on the display unit 13.

Configuration of Sensor

Next, the configuration of the sensor 20 shown in FIG. 1 will be described using FIGS. 2A and 2B. FIG. 2A is a top view of the sensor in the embodiment of the present invention, and FIG. 2B is a cross-sectional view taken along cutting line A-A shown in FIG. 2A.

Figure 2A:
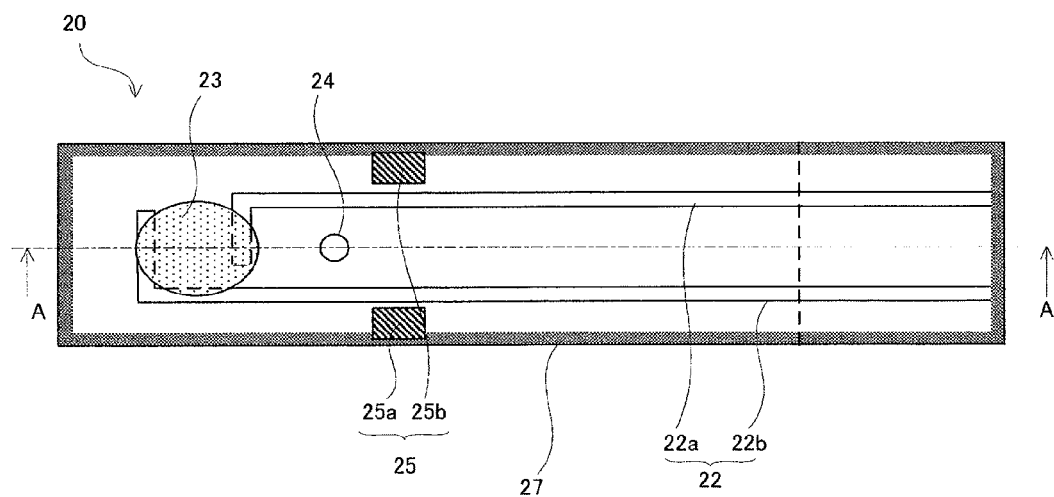
FIG. 2A is a top view of a sensor according to an embodiment of the present invention.
Figure 2B:
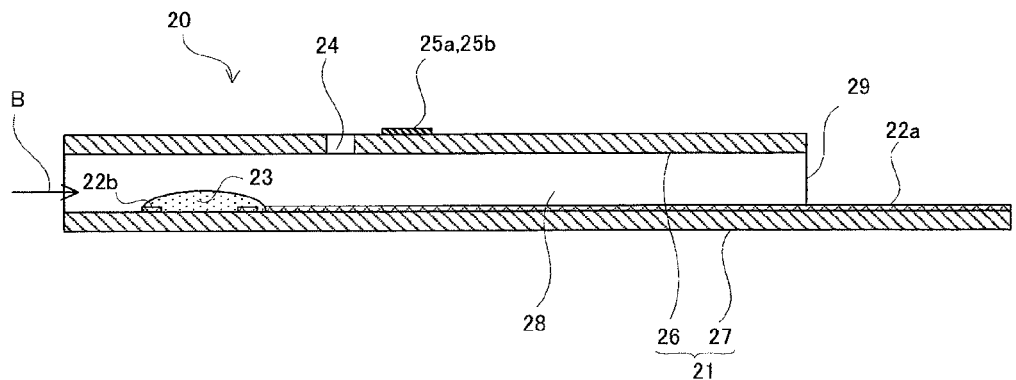
FIG. 2B is a cross-sectional view taken along cutting line A-A shown in FIG. 2A.

As shown in FIGS. 2A and 2B, the sensor 20 includes a substrate 21 that includes an upper substrate 26 and a lower substrate 27, and an electrode 22 for measurement that is provided on the lower substrate 27. Also, the upper substrate 26, the lower substrate 27, and the electrode 22 are formed by an optically transparent member. In the present embodiment, human blood is used as the sample.

According to the sensor 20 having such a configuration, it is possible to cause the sensor 20 to shine by illuminating the sensor 20 itself, and thus, for example, as a result of changing the emission mode of light at that time in accordance with the measurement result or the like, the measurement result or the like can be intuitively understood due to light emitted from the sensor 20. Also, because the user often pays attention to the sensor 20 when supplying a sample to the sensor 20, usability for him or her is increased by notifying the measurement result or the like by causing the sensor 20 itself to shine. Furthermore, because it is not necessary to provide a display or the like that can emit light of a plurality of colors, an increase in manufacturing cost can be suppressed. Hereinafter, a more specific configuration of the sensor 20 will be described.

The sensor 20 further includes a reagent 23 and an air opening 24. Also, in addition to the upper substrate 26 and the lower substrate 27, the substrate 21 further has an information display unit 25, and a spacer 29 such as a side wall or the like that is inserted between the upper substrate 26 and the lower substrate 27. Also, the electrode 22 is formed on the lower substrate 27, and has a pair of electrodes 22a and 22b. Also, the space formed by the spacer 29 between the upper substrate 26 and the lower substrate 27 corresponds to a flow passage 28.

The reagent 23 is applied so as to extend over the electrodes 22a and 22b. It should be noted that although the reagent 23 is applied on the electrodes 22a and 22b in this example, it is sufficient that the reagent 23 is in contact with at least one of the electrodes.

Also, examples of the reagent 23 include oxidoreductases such as glucose oxidase (GOD) and glucose dehydrogenase (GDH), and potassium ferricyanide and hexaammineruthenium chloride that serve as a mediator.

The flow passage 28 guides a sample introduced from the outside to the reagent 23. The air opening 24 is formed in the upper substrate 26, and allows the sample that has been supplied from the tip portion of the sensor 20 in the direction of an arrow B shown in FIG. 2B, for example, to smoothly flow in the flow passage 28.

The upper substrate 26 is formed to be shorter than the lower substrate 27 in the longitudinal direction, and portions of the electrodes 22a and 22b are exposed. This is for, as described later, electrically connecting the electrodes 22a and 22b formed on the lower substrate 27 to a connection terminal inside the insertion opening 12.

The upper substrate 26 and the lower substrate 27 are formed by using, for example, polyethylene terephthalate (PET) as an optically transparent member. The electrodes 22a and 22b are formed by using, for example, indium tin oxide (ITO) as an optically transparent member.

More specifically, a film of indium tin oxide is formed on the lower substrate 27 formed by using polyethylene terephthalate, and laser trimming, chemical etching, or the like is performed on the film to form the electrodes 22a and 22b.

A predetermined amount of the reagent 23 is then dropped on the electrodes 22a and 22b, and the spacer 29 is attached using optically transparent double-sided tape or the like to form the flow passage 28. The upper substrate 26 is then attached thereto to produce the sensor 20.

Also, in the present embodiment, it is preferable that the upper substrate 26 and the lower substrate 27 are configured to have a colored edge. It should be noted that it is not necessary for the entire edge to be colored, and a portion of the edge may be colored. Also, a mark for indicating the opening to which the sample is supplied may be formed on a tip portion of the sensor 20.

The information display unit 25 is provided on the upper substrate 26, and displays identification information of the sensor 20. This information display unit 25 displays identification information using a pattern formed by using at least one of a transmitting portion that allows light entering the upper substrate 26 to pass through, and a light-blocking portion that blocks light entering the upper substrate 26.

It should be noted that although the information display unit 25 may be provided on the lower substrate 27, it is preferable that the information display unit 25 is provided at a position where the flow of the sample in the flow passage 28 is not prevented.

Figure 3A:
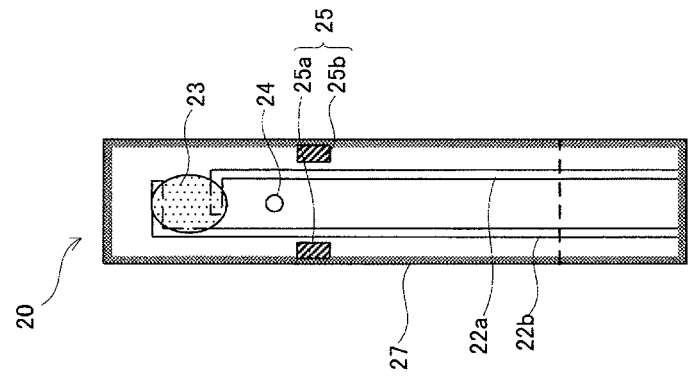
FIGS. 3A to 3C are diagrams showing specific examples of patterns on an information display unit shown in FIGS. 2A and 2B.
Figure 3B:
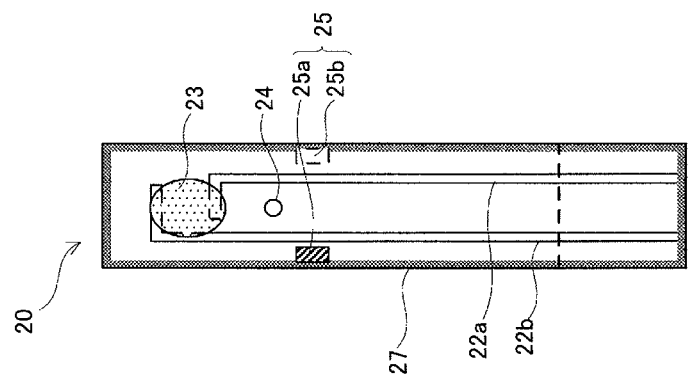
Figure 3C:
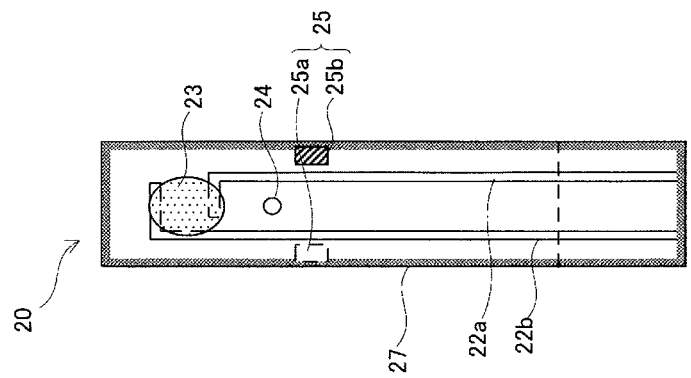

FIGS. 3A to 3C are diagrams showing specific examples of patterns on the information display unit 25 shown in FIGS. 2A and 2B.

The sensor 20 shown in FIGS. 3A to 3C includes two regions 25a and 25b obtained by dividing the information display unit 25 into right and left portions. The information display unit 25 of the sensor 20 shown in FIG. 3A is formed by a left region 25a that is a transmitting portion and a right region 25b that is a light-blocking portion. Also, the information display unit 25 of the sensor 20 shown in FIG. 3B is formed by a left region 25a that is a light-blocking portion and a right region 25b that is a transmitting portion. Also, the information display unit 25 of the sensor 20 shown in FIG. 3C is formed by a left region 25a that is a light-blocking portion and the right region 25b that is a light-blocking portion.

In this manner, as a result of different patterns formed by using at least one of a transmitting portion and a light-blocking portion, the information display unit 25 can display different identification information. Examples of this identification information include the lot number of the sensor 20, the expiration data of the sensor 20, and information relating to sensitivity correction of the sensor 20.

Internal Configuration of Insertion Opening

Figure 4:
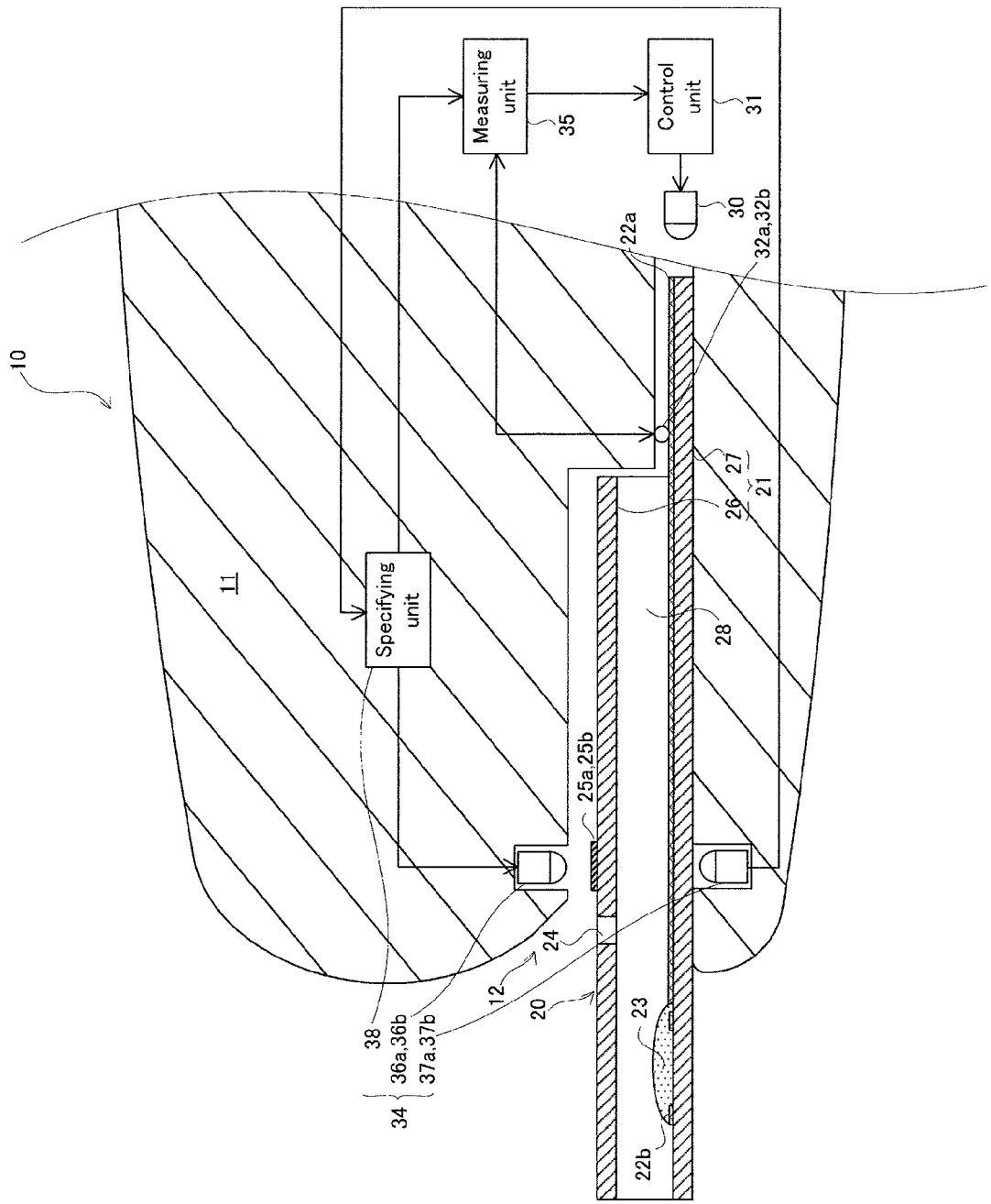
FIG. 4 is a partial enlarged cross-sectional view of the measuring apparatus and the sensor according to the embodiment of the present invention.

Next, the internal configuration of the insertion opening 12 shown in FIG. 1 will be described using FIG. 4. FIG. 4 is a partial enlarged cross-sectional view of the measuring apparatus and the sensor in the embodiment of the present invention.

As shown in FIG. 4, a light source (a first light source) 30, a control unit 31, a pair of connection terminals 32a and 32b, an identification information reading unit 34, and a measuring unit 35 are provided inside the insertion opening 12 of the main body 11. The identification information reading unit 34 includes a pair of a light source (a second light source) 36a and a light source (a second light source) 36b, a pair of light-receiving portions 37a and 37b, and a specifying unit 38.

The connection terminals 32a and 32b are respectively connected to the electrodes 22a and 22b of the sensor 20 in a state in which the sensor 20 is inserted into the insertion opening 12. It should be noted that depiction of the connection terminal 32b is omitted in FIG. 4.

The light source 36a and the light-receiving portion 37a are provided at a position corresponding to the left region 25a of the information display unit 25 of the sensor 20 in a state in which the sensor 20 is inserted into the insertion opening 12. Also, although depiction is omitted in FIG. 4, the light source 36b and the light-receiving portion 37b are provided at a position corresponding to the right region 25b of the information display unit 25 of the sensor 20 in a state in which the sensor 20 is inserted into the insertion opening 12.

The specifying unit 38 controls light emission from the light sources 36a and 36b. Also, the specifying unit 38 acquires a result of the light-receiving portions 37a and 37b receiving light, and specifies identification information of the sensor 20 based on the acquired light reception result.

The measuring unit 35 measures an electric current value by electrochemically measuring the reagent 23 that has reacted with the sample, and outputs the measurement result to the control unit 31. The control unit 31 changes the emission mode of light emitted from the light source 30 in accordance with the measurement result acquired from the measuring unit 35. It should be noted that the emission modes are set by changing at least one of the light wavelength, the lighting interval, and the like.

Operation

Next, operations when the measuring apparatus 10 and the sensor 20 in the embodiment of the present invention are used will be described with reference to drawings.

Figure 5:
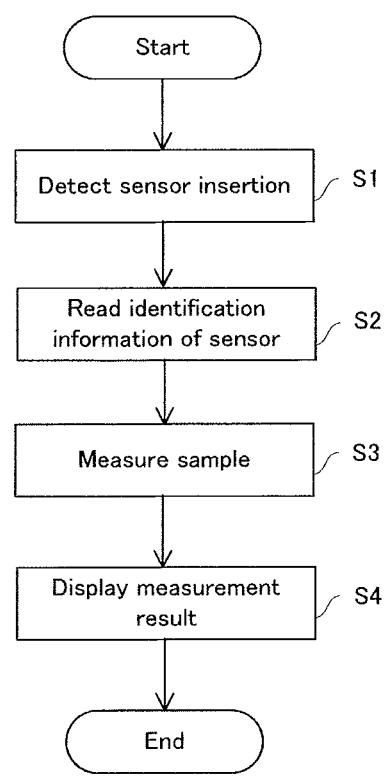
FIG. 5 is a flowchart for describing a flow of operations when the measuring apparatus and the sensor according to the embodiment of the present invention are used.
Figures 6A, 6B, 6C:
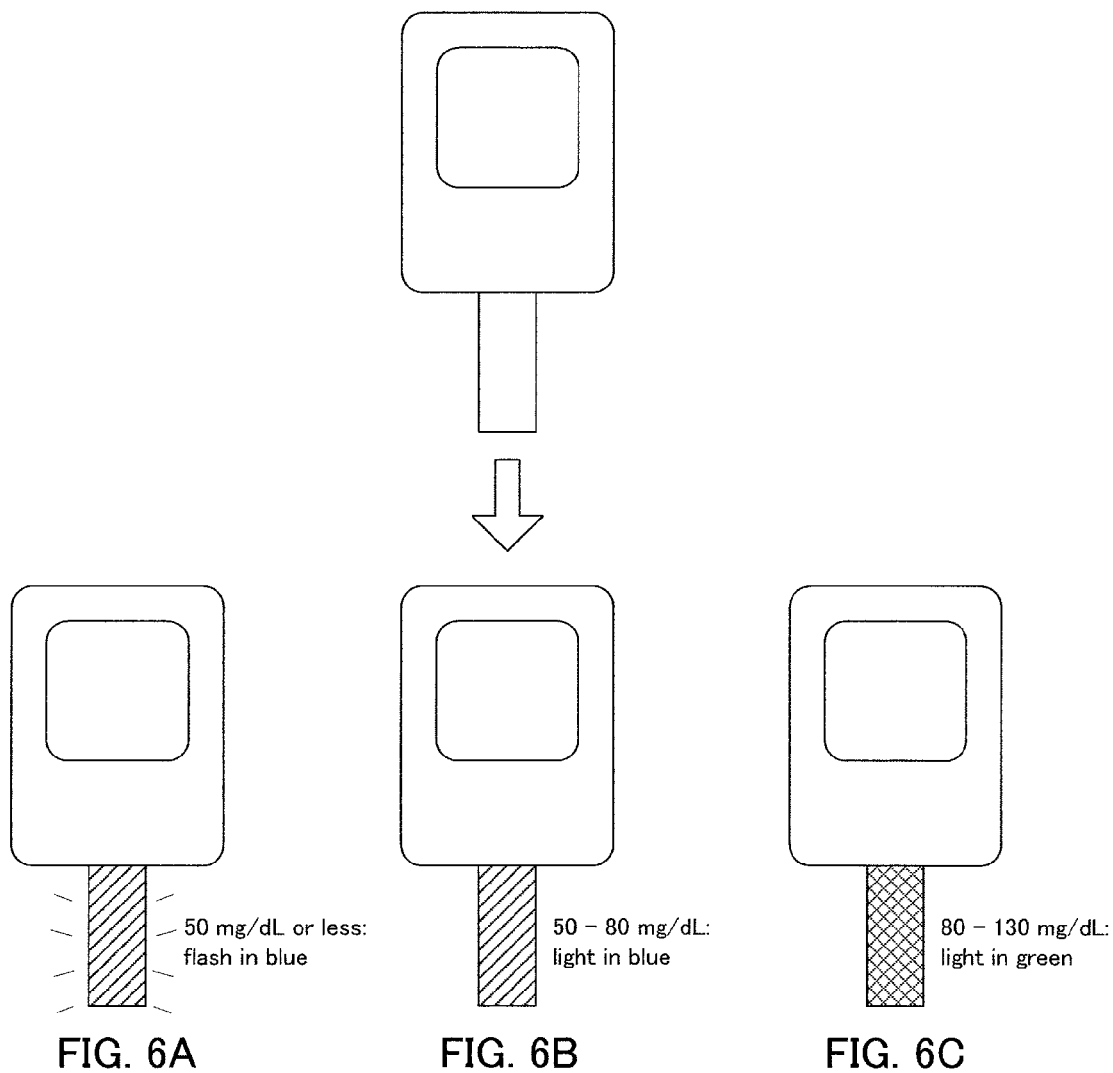
FIGS. 6A to 6E are diagrams showing specific examples of emission modes of light emitted in accordance with a result of measurement performed by a measuring unit shown in FIG. 4.
Figures 6D, 6E:
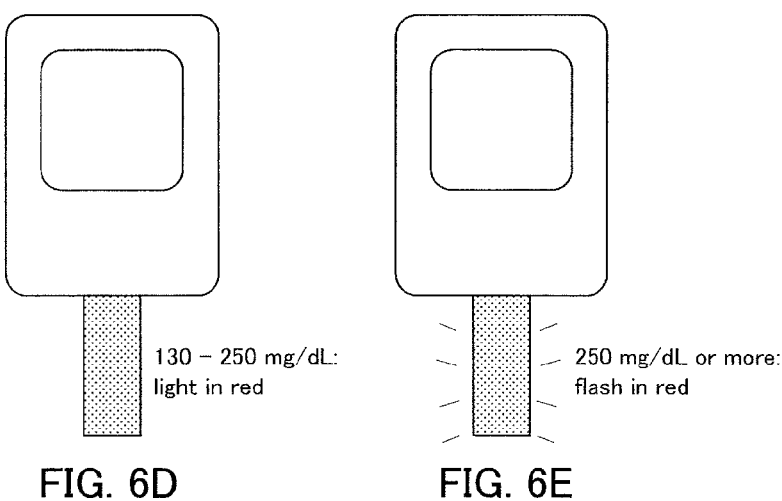

FIG. 5 is a flowchart for describing a flow of operations when the measuring apparatus and the sensor in the embodiment of the present invention are used.

With reference to FIGS. 4 and 5 described above, first, it is assumed that, for example, a user of the measuring apparatus 10 grips the sensor 20 in his or her hand, and inserts the sensor 20 into the insertion opening 12 of the main body 11.

Thereafter, when the electrodes 22a and 22b are respectively connected to the connection terminals 32a and 32b, a switch (not shown) of the main body 11 is turned on and the measuring apparatus 10 is started, as a result of which the main body 11 detects that the sensor 20 is inserted (step S1).

Next, when the main body detects that the sensor 20 is inserted, the specifying unit 38 causes the light sources 36a and 36b to emit light. Thereafter, the specifying unit 38 specifies identification information of the sensor 20 that has been inserted into the insertion opening 12 based on light received by the light-receiving portions 37a and 37b.

For example, it is assumed that the left region 25a of the information display unit 25 is a transmitting portion, and the right region 25b thereof is a light-blocking portion. In this case, the light-receiving portion 37a is irradiated with light emitted from the light source 36a, and receives light that has passed through the upper substrate 26 and the lower substrate 27. On the other hand, light emitted from the light source 36b is blocked at the right region 25b, and therefore, the light-receiving portion 37b does not receive light from the light source 36b.

The specifying unit 38, for example, stores light reception results from the light-receiving portions 37a and 37b and pieces of identification information of the sensor 20 in association with each other in advance. Accordingly, for example, the specifying unit 38 can specify identification information of the sensor 20 that has been inserted into the insertion opening 12 by acquiring a light-reception result indicating that the light-receiving portion 37a has received light and the light-receiving portion 37b has not received light (step S2).

Next, the specifying unit 38 outputs the specified identification information of the sensor 20 to the measuring unit 35. Thereafter, the measuring unit 35 measures a sample using the acquired identification information. Specifically, the measuring unit 35 selects a calibration curve that is to be used for measurement based on the identification information of the sensor 20 from among a plurality of calibration curves prepared in advance. Thereafter, the measuring unit 35 measures an electric current value obtained by electrochemically measuring the reagent 23 that has reacted with the sample via the electrodes 22a and 22b and the connection terminals 32a and 32b. The measuring unit 35 then applies the measured value to the selected calibration curve to calculate the blood glucose level of the user (step S3).

It should be noted that reading of identification information of the sensor 20 by the identification information reading unit 34 (step S2) and measurement of a sample by the measuring unit 35 (step S3) may be performed in the opposite order. Specifically, for example, the measuring unit 35 may use identification information of the sensor 20 that has been read by the identification information reading unit 34 after measuring a sample to correct the measurement result, or the like.

Next, the measuring unit 35 outputs the measurement result to the control unit 31. Thereafter, the control unit 31 causes the display unit 13 (see FIG. 1) to display the acquired measurement result. Furthermore, the control unit 31 changes the emission mode of light emitted from the light source 30 in accordance with the measurement result. Accordingly, the sensor 20 emits light in a mode that corresponds to the measurement result (step S4). This will be described in detail below using FIGS. 6A to 6E.

It should be noted that, for example, in the case where it is difficult for the light source 30 to be provided near the insertion opening 12 due to the space inside the main body 11, a configuration is possible in which an optical fiber or the like is used to transmit light from the light source 30 to the insertion opening 12, or a mirror or the like is used to reflect light from the light source 30 to guide the light from the light source 30 to the insertion opening 12.

FIGS. 6A to 6E are diagrams showing specific examples of emission modes of light emitted in accordance with a result of measurement performed by the measuring unit shown in FIG. 4.

For example, a plurality of LEDs are provided inside the main body 11 as the light source 30 so as to emit light of a plurality of colors such as blue, green, and red. In addition, the control unit 31 emits light toward the sensor 20 in various emission modes by switching the LED that is operated in accordance with the measurement result.

Specifically, as shown in FIGS. 6A to 6E, for example, in the case where the blood glucose level is 50 mg/dL or less, the control unit 31 performs control such that a blue LED flashes. Accordingly, the sensor 20 in which the substrate 21 and the electrode 22 are formed by an optically transparent member flashes in blue (see FIG. 6A). Also, for example, in the case where the blood glucose level is 50 to 80 mg/dL or less, the control unit 31 performs control such that the blue LED is lit. Accordingly, the sensor 20 is lit in blue (see FIG. 6B).

Also, for example, in the case where the blood glucose level is 80 to 130 mg/dL or less, the control unit 31 performs control such that a green LED is lit. Accordingly, the sensor 20 is lit in green (see FIG. 6C). Also, for example, in the case where the blood glucose level is 130 to 250 mg/dL or less, the control unit 31 performs control such that a red LED is lit. Accordingly, the sensor 20 is lit in red (see FIG. 6D). Furthermore, for example, in the case where the blood glucose level is 250 mg/dL or more, the control unit 31 performs control such that the red LED flashes. Accordingly, the sensor 20 flashes in red (see FIG. 6E).

It should be noted that as described above, because the control unit 31 can cause the sensor 20 to emit light in various emission modes in accordance with the measurement result to notify the user of the measurement result, a configuration is possible in which the measurement result is not displayed by the display unit 13.

Also, for example, a reflection board or the like may be provided on side faces of the upper substrate 26 and the lower substrate 27 in order to reflect light emitted toward the sensor 20. In such a configuration, because the emission mode of light emitted from the light source 30 can be easily checked, the measurement result can be more easily checked.

Also, for example, as a result of the upper substrate 26 and the lower substrate 27 being formed using translucent polyethylene terephthalate, the emission mode such as the light color, the light interval, and the like of the light source 30 can be more easily checked, compared with a case in which the upper substrate 26 and the lower substrate 27 are formed using a transparent member.

Effects

As described above, the sensor 20 according to the embodiment of the present invention includes the substrate 21 that includes the upper substrate 26 and the lower substrate 27, and the electrode 22 that is provided on the lower substrate 27, and the upper substrate 26, the lower substrate 27, and the electrode 22 are formed by an optically transparent member.

Accordingly, it is possible to cause the sensor to shine by illuminating the sensor itself, and thus, for example, as a result of changing the emission mode of light at that time in accordance with the measurement result or the like, the measurement result or the like can be intuitively understood due to light emitted from the sensor. Also, because a user often pays attention to the sensor 20 when supplying a sample to the sensor 20, usability for him or her is further increased by notifying the measurement result or the like by causing the sensor 20 to shine. Furthermore, because it is not necessary to provide a display or the like that can emit light of a plurality of color, an increase in manufacturing cost can be suppressed.

Also, in the sensor 20 in the embodiment of the present invention, the substrate 21 further includes the information display unit 25 that displays identification information of the sensor 20. Also, the information display unit 25 displays identification information using a pattern formed using at least one of the transmitting portion that allows light entering the substrate 21 to pass through and the light-blocking portion that blocks light entering the substrate 21.

According to the sensor 20 having such a configuration, for example, because identification wiring can be formed in the same manufacturing step as that for sensor wiring, identification information can be displayed for each sensor 20 using a simple configuration without making holes in a substrate 21 using a different pattern.

Also, in the sensor 20 in the embodiment of the present invention, at least one portion of an edge of the substrate 21 is colored.

According to the sensor 20 having such a configuration, the sensor 20 can be caused to stand out even if the substrate 21 and the electrode 22 are formed by an optically transparent member, and thus, it is possible to prevent the sensor 20 from being lost and to easily see the shape of the sensor 20.

Variation 1

(a) Part 1

Figure 7:
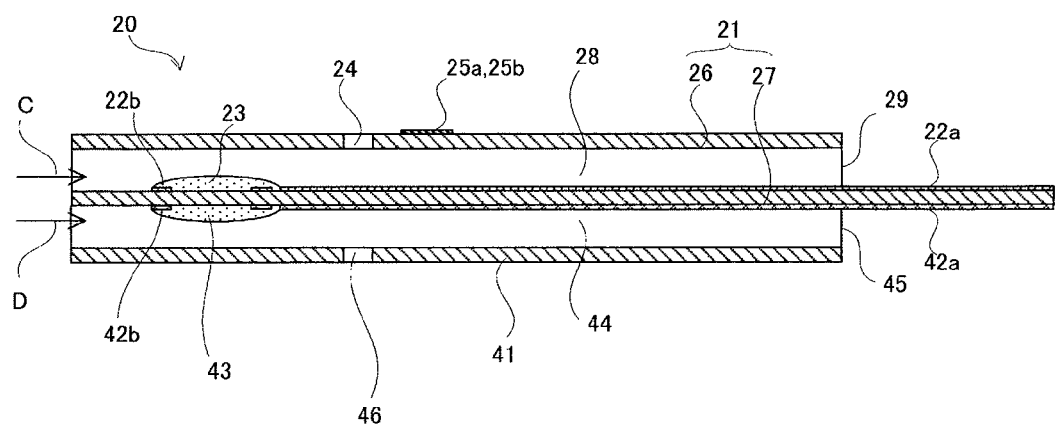
FIG. 7 is a cross-sectional view showing a configuration of a variation 1 (part 1) of the sensor according to the embodiment of the present invention.

FIG. 7 is a cross-sectional view showing the configuration of a variation 1 (part 1) of the sensor according to the embodiment of the present invention.

As shown in FIG. 7, the variation 1 (part 1) of the sensor 20 according to the embodiment of the present invention further includes a second upper substrate 41, compared with the sensor 20 shown in FIGS. 2A and 2B. An air opening 46 is formed in the second upper substrate 41.

Also, in addition to electrodes (first electrodes) 22a and 22b provided on the upper face of the lower substrate 27 and a reagent 23, a pair of electrodes (second electrodes) 42a and 42b, a reagent 43, and a spacer 45 such as a side wall inserted between the second upper substrate 41 and the lower substrate 27 are further provided on a lower face of the lower substrate 27. Also, a space that is formed by the spacer 45 between the second upper substrate 41 and the lower substrate 27 corresponds to a flow passage 44.

In other words, a user can supply a sample from either an arrow C direction or an arrow D direction shown in FIG. 7. Moreover, in the case where a sample is supplied in the direction of the arrow C, the sample flows inside the flow passage 28, and in the case where a sample is supplied in the direction of the arrow D, the sample flows inside the flow passage 44.

Similarly to the upper substrate 26, the second upper substrate 41 is formed by an optically transparent member, and is formed to be shorter than the lower substrate 27 in the longitudinal direction. Thus, portions of the electrodes 42a and 42b are exposed.

Accordingly, in the case where the sensor 20 is inserted into the insertion opening 12 so that the upper substrate 26 is an upper face, the electrodes 22a and 22b are electrically connected to the connection terminals 32a and 32b inside the insertion opening 12. On the other hand, in the case where the sensor 20 is inserted into the insertion opening 12 so that the second upper substrate 41 is the upper face, the electrodes 42a and 42b are electrically connected to the connection terminals 32a and 32b inside the insertion opening 12.

In this manner, as a result of flow passages and electrodes being provided on both the upper face and the lower face of the lower substrate 27, a user can check that a sample has been introduced by suction from either the front side or the back side when using the sensor 20. Thus, it is possible to provide the sensor 20 and the measuring apparatus 10 whose usability for a user is increased.

Figure 8:
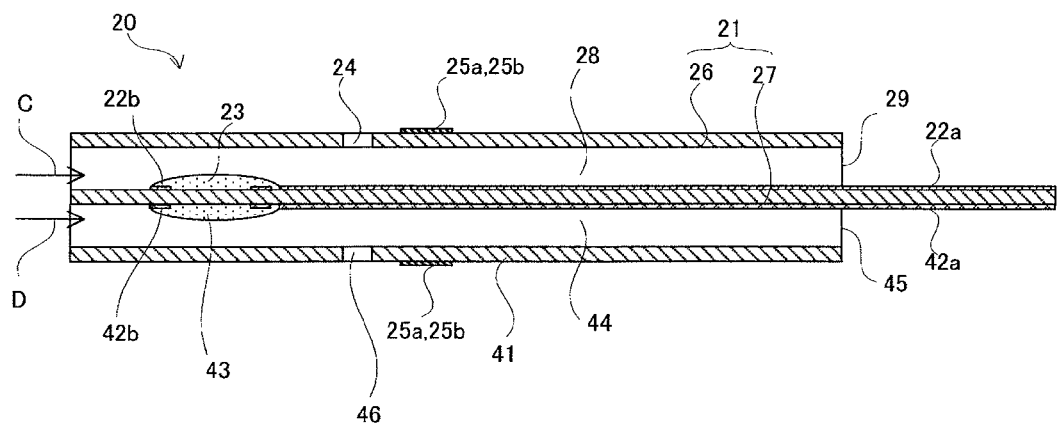
FIG. 8 is a cross-sectional view showing a configuration of another example of the variation 1 (part 1) of the sensor according to the embodiment of the present invention.

FIG. 8 is a cross-sectional view showing the configuration of another example of the variation 1 (part 1) of the sensor according to the embodiment of the present invention.

As shown in FIG. 8, the variation 1 (part 1) of the sensor 20 according to the embodiment of the present invention is further provided with regions 25a and 25b of an information display unit 25 on the second upper substrate 41, compared with the variation of the sensor 20 shown in FIG. 7.

Accordingly, a user can check identification information of the sensor 20 from either the front side or the back side.

(b) Part 2

Figure 9:
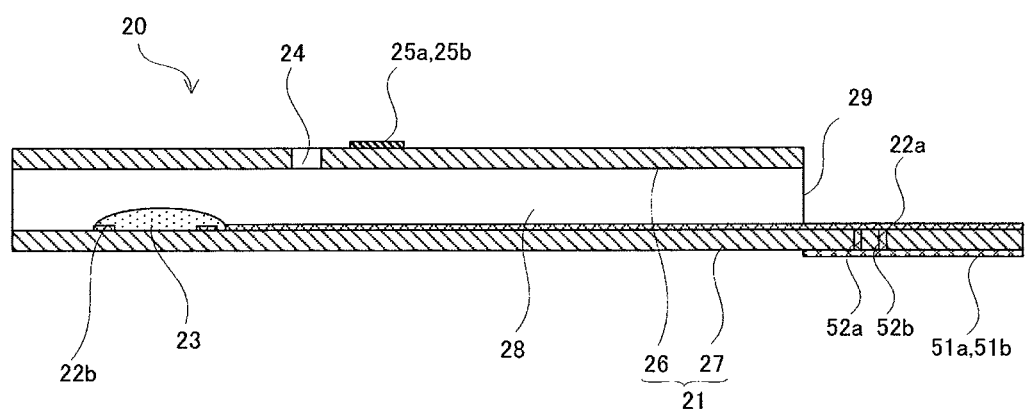
FIG. 9 is a cross-sectional view showing a configuration of the variation 1 (part 2) of the sensor according to the embodiment of the present invention.

FIG. 9 is a cross-sectional view showing the configuration of the variation 1 (part 2) of the sensor according to the embodiment of the present invention.

Also, electrodes (second electrodes) 51a and 51b may be provided on the lower face of the lower substrate 27 at positions corresponding to portions of the electrodes (first electrodes) 22a and 22b that are to be connected to the connection terminals 32a and 32b when the sensor 20 is inserted into the insertion opening 12 of the main body 11, that is, portions of the electrodes 22a and 22b that are exposed from the upper substrate 26.

In such a configuration, for example, through holes 52a and 52b are formed in the lower substrate 27, and a conductive film is provided on the internal walls of these through holes 52a and 52b. The conductive film provided on the inner wall of the through hole 52a allows the electrodes 22a and 51b to be electrically connected to each other, and the conductive film provided on the inner wall of the through hole 52b allows the electrodes 22b and 51b to be electrically connected to each other.

Accordingly, in the case where the sensor 20 is inserted into the insertion opening 12 so that the upper substrate 26 is the upper face, the electrodes 22a and 22b are electrically connected to the connection terminals 32a and 32b inside the insertion opening 12. On the other hand, in the case where the sensor 20 is inserted into the insertion opening 12 so that the lower substrate 27 is the upper face, the electrodes 51a and 51b are electrically connected to the connection terminals 32a and 32b inside the insertion opening 12 via the through holes 52a and 52b and the electrodes 22a and 22b.

According to the sensor having such a configuration, similarly to the above-described variation 1 (part 1), a user can check that a sample has been introduced by suction from either the front side or the back side when using the sensor 20, the usability for him or her is further increased.

Furthermore, with a configuration in which the electrodes 22a and 22b are electrically connected to the electrodes 51a and 51b via the through holes 52a and 52b, it is possible to realize the sensor 20 using a simple configuration, in which a plurality of flow passages do not need to be provided and in which it is possible to check that a sample has been introduced by suction from either the front side or the back side when the sensor 20 is used.

Figure 10:
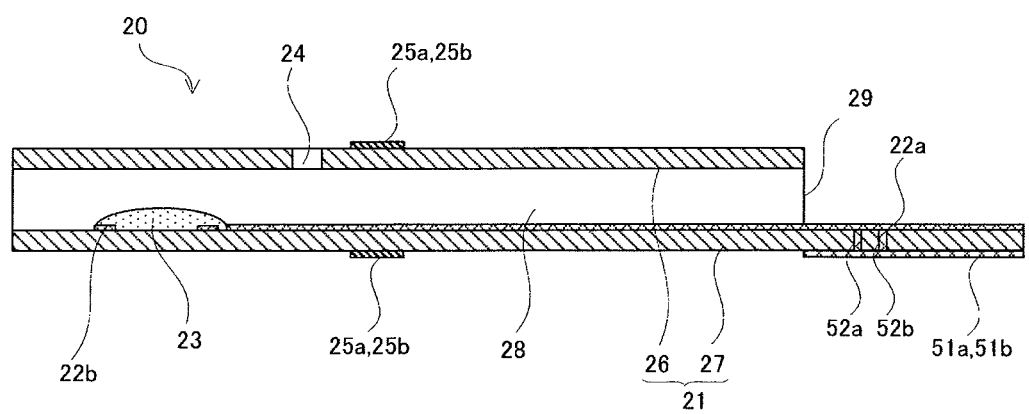
FIG. 10 is a cross-sectional view showing a configuration of another example of the variation 1 (part 2) of the sensor according to the embodiment of the present invention.

FIG. 10 is a cross-sectional view showing the configuration of another example of the variation 1 (part 2) of the sensor according to the embodiment of the present invention.

As shown in FIG. 10, the variation 1 (part 2) of the sensor 20 according to the embodiment of the present invention is further provided with regions 25a and 25b of the information display unit 25 on the lower substrate 27, compared with the variation of the sensor 20 shown in FIG. 9. Accordingly, a user can check identification information of the sensor 20 from either the front side or the back side.

Variation 2

Figure 11:
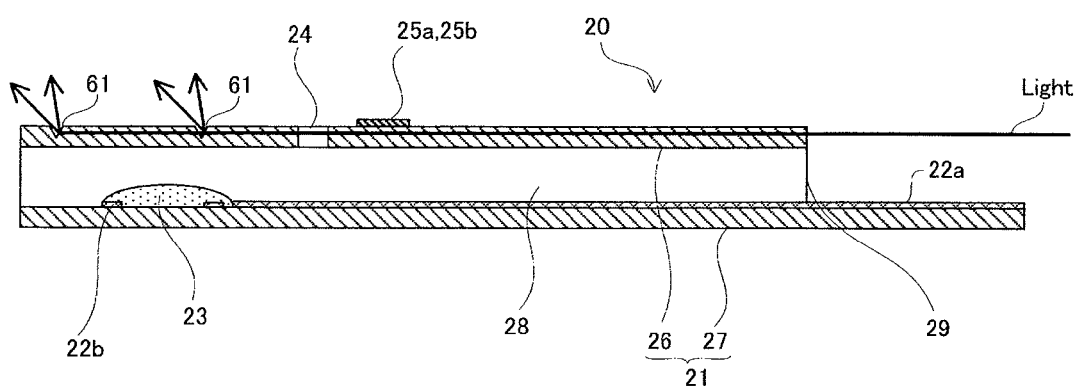
FIG. 11 is a cross-sectional view of a variation 2 of the sensor according to the embodiment of the present invention.

FIG. 11 is a cross-sectional view of a variation 2 of the sensor according to the embodiment of the present invention.

As shown in FIG. 11, the variation 2 of the sensor 20 according to the embodiment of the present invention is provided with reflective portions 61 on the upper substrate 26. These reflective portions 61 have, for example, a groove shape that is formed so as to expand toward the upper face of the upper substrate 26. Accordingly, when light is emitted from the light source 30 toward the sensor 20, the light is reflected toward the upper face of the upper substrate 26 in the reflective portions 61 of the upper substrate 26.

Figure 12:
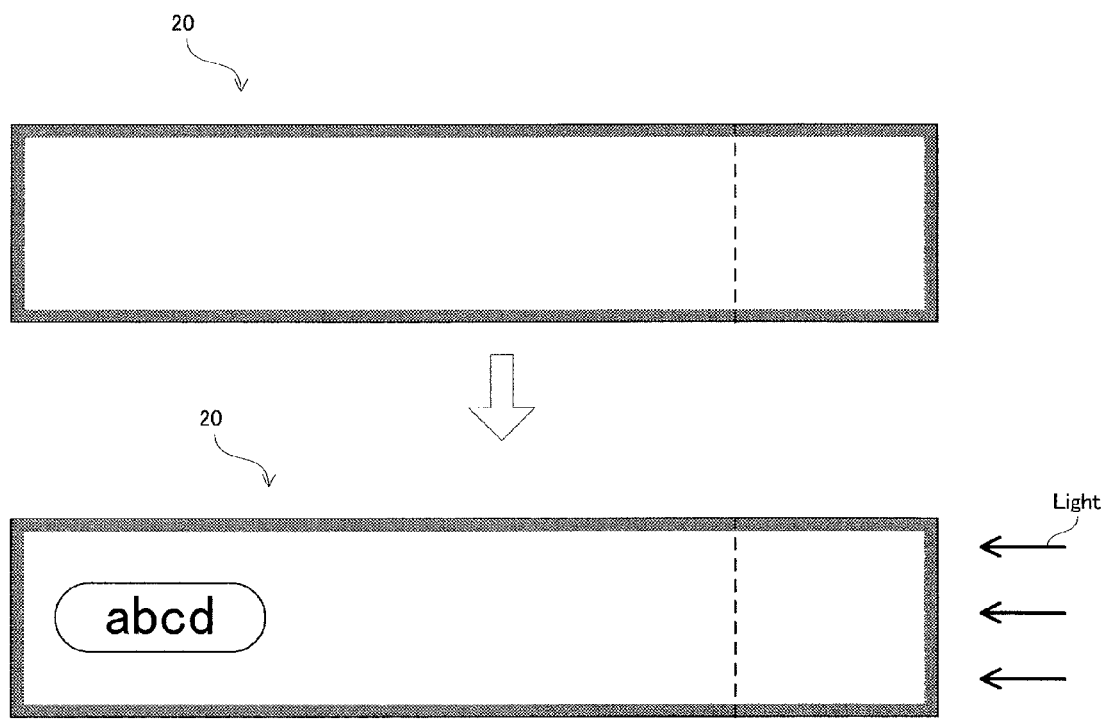
FIG. 12 is an example of a top view of the sensor when the sensor shown in FIG. 11 is irradiated with light.

FIG. 12 is an example of a top view of the sensor when the sensor shown in FIG. 11 is irradiated with light.

As described above, as a result of light being reflected toward the upper face of the upper substrate 26 in the reflective portions 61, for example, as shown in FIG. 12, it is possible to display information such as letters or figures relating to the sensor 20.

In this manner, with the configuration in which the substrate 21 includes the reflective portions 61 that reflect light entering the substrate 21, and the reflective portions 61 display information relating to the sensor 20 by reflecting light, even in a case where a user has poor eyesight, he or she can easily check information relating to the sensor 20.

Variation 3

In a variation 3 of the measuring apparatus 10 according to the embodiment of the present invention, for example, the control unit 31 may cause the light source 30 to emit light in various emission modes in accordance with the condition under which the measuring apparatus 10 is used by a user.

Figure 13A:
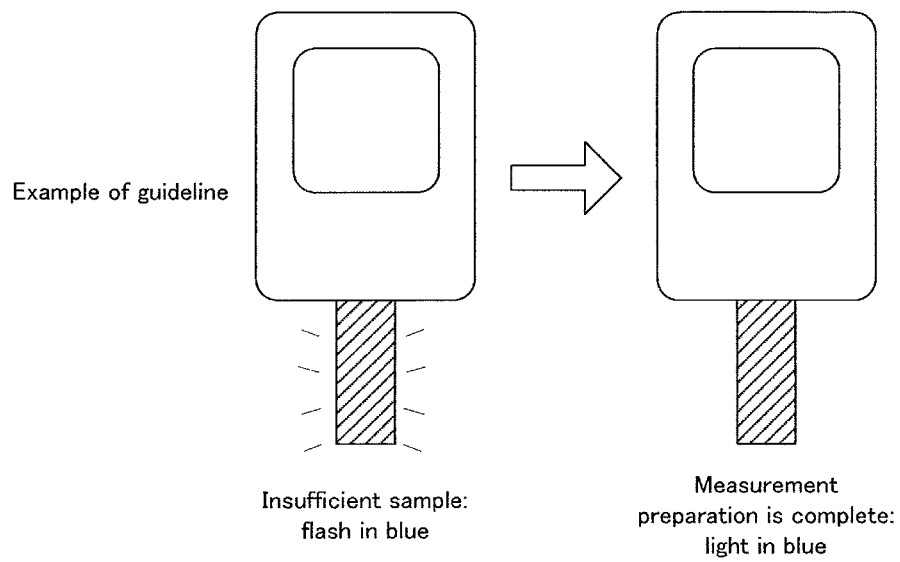
FIGS. 13A and 13B are diagrams showing specific examples of emission modes of light emitted in accordance with the condition under which the measuring apparatus is used.
Figure 13B:
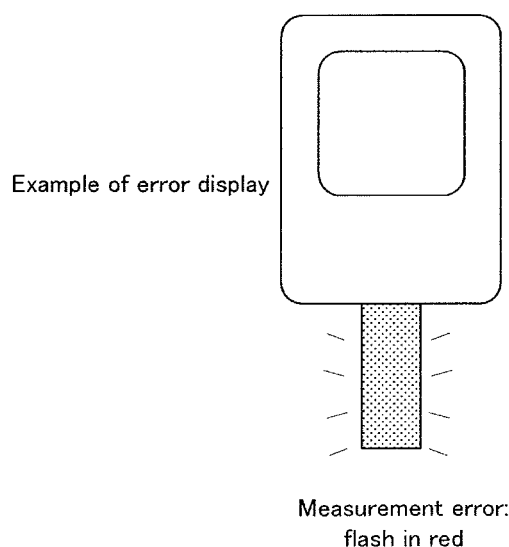

FIGS. 13A and 13B are diagrams showing specific examples of emission modes of light emitted in accordance with the condition under which the measuring apparatus is used.

For example, as shown in FIG. 13A, the control unit 31 performs control such that a blue LED flashes when the sensor 20 is inserted into the main body 11. Accordingly, the sensor 20 flashes in blue. The control unit 31 then continues to cause the blue LED to flash until a sufficient amount of a sample for measurement has been dropped onto the sensor 20. Thereafter, for example, when a sufficient amount of a sample for measurement has been dropped onto the sensor 20, the control unit 31 switches the blue LED from flashing to being lit. Accordingly, the sensor 20 is lit in blue.

Also, for example, as shown in FIG. 13B, in the case where an error occurred such as the case where a mistake is made in the procedure in which a user uses the sensor 20, or case where appropriate measurement cannot be performed, the control unit 31 performs control such that a red LED flashes. Accordingly, the sensor 20 flashes in red, and thus, it is possible to notify the user of an error. It should be noted that the control unit 31 may have a configuration so as to cause the sensor 20 to emit light in a different mode in accordance with types of errors.

According to such a configuration, as a result of a user checking the emission mode of the sensor 20, he or she can understand whether or not the amount of the dropped sample is appropriate, or whether a mistake was made in the usage procedure. Also, because a user often pays attention to the sensor 20 when the sample is dropped, with the measuring apparatus 10 that allows him or her to check the appropriate amount of the sample or the appropriate usage procedure by checking light emitted from the sensor 20, usability for him or her can be further improved.

Also, compared with an error notification given by outputting sound, limitation on the usage location is reduced, as a result of which usability for a user can be further improved.

As described above, the present invention is useful in the field of medical devices, in particular, small mobile medical devices.

Although the present invention has been described and illustrated in detail, it is clearly understood that the same is by way of illustration and example only and is not to be taken by way of limitation, the scope of the present invention being interpreted by the terms of the appended claims.

What is claimed is:

1. A sensor configured for measuring biological information on a user, comprising:
   a substrate comprising an upper substrate and a lower substrate; and
   an electrode provided on the lower substrate,
   wherein the upper substrate, the lower substrate, and the electrode are formed of an optically transparent member, and
   wherein the substrate displays identification information of the sensor by a pattern formed by using at least one of a transmitting portion provided on the surface of the substrate that allows light entering the substrate to pass through and a light-blocking portion provided on the surface of the substrate that blocks light entering the substrate.

2. The sensor according to claim 1, wherein
   the electrode comprises a first electrode formed on a first surface of the substrate and a second electrode formed on a second surface of the substrate opposite the first surface, and
   the first electrode and the second electrode are electrically connected to each other via a through hole that passes through the substrate.

3. The sensor according to claim 1, wherein the reflective portion contains a groove formed on the surface of the substrate and reflects light entering the substrate at the groove.

4. The sensor according to claim 1, wherein at least a portion of an edge of the substrate is colored.

* * * * *